US009119714B2

(12) United States Patent
Shandas et al.

(10) Patent No.: US 9,119,714 B2
(45) Date of Patent: Sep. 1, 2015

(54) SHAPE MEMORY POLYMER PROSTHETIC MEDICAL DEVICE

(75) Inventors: Robin Shandas, Boulder, CO (US); Avery Nelson, Boulder, CO (US); Bryan Rech, Boulder, CO (US); Devatha P. Nair, Lakewood, CO (US); Michael B. Lyons, Boulder, CO (US); Jeffrey Paul Castleberry, Longmont, CO (US); Timothy Francis Scott, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 724 days.

(21) Appl. No.: 12/608,714

(22) Filed: Oct. 29, 2009

(65) Prior Publication Data

US 2010/0152839 A1    Jun. 17, 2010

Related U.S. Application Data

(60) Provisional application No. 61/109,295, filed on Oct. 29, 2008.

(51) Int. Cl.
*A61F 2/24* (2006.01)
*B29C 61/06* (2006.01)
(Continued)

(52) U.S. Cl.
CPC ............. *A61F 2/2412* (2013.01); *A61F 2/2475* (2013.01); *B29C 61/0608* (2013.01);
(Continued)

(58) Field of Classification Search
CPC ... A61F 2/2418; A61F 2/2412; A61F 2/2415; A61F 2/2475; A61F 2/82; A61F 2/88; A61F 2/915; A61F 2/0063; A61F 2/02; A61F 2/07; A61F 2/24; A61F 2/2445; A61F 2/2463; A61F 2/848
USPC ................................................ 623/2.11–2.42
See application file for complete search history.

(56) References Cited

U.S. PATENT DOCUMENTS 4,606,336 A    8/1986 Zeluff
4,950,258 A    8/1990 Kawai et al.
(Continued)

FOREIGN PATENT DOCUMENTS

CA    2527976    12/2004
WO    WO 2008051254    5/2008

OTHER PUBLICATIONS

Author Unknown, Codman & Shurtleff, Inc., "Trufill DCS Orbit Detachable Coil System", 2000-2010, pp. 2, http://www.codman.com/DePuy/products/Products/neurovascular/ trufillorbit/index.html.
(Continued)

*Primary Examiner* — David Isabella
*Assistant Examiner* — Ann Schillinger
(74) *Attorney, Agent, or Firm* — Dorsey & Whitney LLP (57) ABSTRACT

A prosthetic medical device is formed by the combination of a biological tissue a shape memory polymer structure. The biological tissue provides an in-situ physiological function of the device. The shape memory polymer provides a capability for minimizing the device profile during insertion and then deploying after placement into a memory shape that achieves suitable mechanical structure and stability within an anatomical lumen or cavity. This configuration may be applied to form various prosthetic devices including aortic, mitral, and tricuspid valves in the heart; venous valves; anti-reflux valves for the lower esophageal sphincter; and other biological valve structures. Alternatively, an entirely non-biologic implementation using only shape memory polymer-based structures may be used as a prosthetic valve device.

5 Claims, 8 Drawing Sheets

(51) Int. Cl.
  *A61F 2/88* (2006.01)
  *B29L 31/00* (2006.01)
(52) U.S. Cl.
  CPC ............. *A61F2/2418* (2013.01); *A61F 2/2436* (2013.01); *A61F 2/2469* (2013.01); *A61F 2/88* (2013.01); *B29L 2031/7534* (2013.01); *Y10T 156/1031* (2015.01)

(56) References Cited

U.S. PATENT DOCUMENTS

| | | | |
|---|---|---|---|
| 4,994,069 | A | 2/1991 | Ritchart et al. |
| 5,163,952 | A | 11/1992 | Froix |
| 5,258,020 | A | 11/1993 | Froix |
| 5,599,291 | A | 2/1997 | Balbierz et al. |
| 5,674,241 | A | 10/1997 | Bley et al. |
| 5,674,242 | A | 10/1997 | Phan et al. |
| 5,964,744 | A | 10/1999 | Balbierz et al. |
| 6,090,125 | A | 7/2000 | Horton |
| 6,160,084 | A | 12/2000 | Langer et al. |
| 6,165,198 | A | 12/2000 | McGurk et al. |
| 6,248,129 | B1 | 6/2001 | Froix |
| 6,281,262 | B1 | 8/2001 | Shikinami |
| 6,388,043 | B1 | 5/2002 | Langer et al. |
| 6,440,164 | B1 * | 8/2002 | DiMatteo et al. ............ 623/1.24 |
| 6,550,480 | B2 | 4/2003 | Feldman et al. |
| 6,551,305 | B2 | 4/2003 | Ferrera et al. |
| 6,616,617 | B1 | 9/2003 | Ferrera et al. |
| 6,712,810 | B2 | 3/2004 | Harrington et al. |
| 6,720,402 | B2 | 4/2004 | Langer et al. |
| 6,740,094 | B2 | 5/2004 | Maitland et al. |
| 6,746,461 | B2 | 6/2004 | Fry |
| 6,887,266 | B2 | 5/2005 | Williams et al. |
| 7,115,691 | B2 | 10/2006 | Alvarado et al. |
| 7,208,550 | B2 | 4/2007 | Mather et al. |
| 7,217,744 | B2 | 5/2007 | Lendlein et al. |
| 2002/0062130 | A1 * | 5/2002 | Jugenheimer et al. ......... 606/142 |
| 2003/0083735 | A1 | 5/2003 | Denardo et al. |
| 2004/0030062 | A1 | 2/2004 | Mather et al. |
| 2004/0030405 | A1 * | 2/2004 | Carpentier et al. ......... 623/23.72 |
| 2004/0093075 | A1 * | 5/2004 | Kuehne ......................... 623/1.15 |
| 2004/0122174 | A1 | 6/2004 | Mather et al. |
| 2005/0033163 | A1 | 2/2005 | Duchon et al. |
| 2006/0036045 | A1 | 2/2006 | Wilson et al. |
| 2006/0041089 | A1 | 2/2006 | Mather et al. |
| 2006/0095134 | A1 | 5/2006 | Trieu et al. |
| 2006/0142794 | A1 | 6/2006 | Lendlein et al. |
| 2006/0206140 | A1 | 9/2006 | Shaolian et al. |
| 2006/0213522 | A1 | 9/2006 | Menchaca et al. |
| 2008/0004692 | A1 | 1/2008 | Henson et al. |
| 2008/0281405 | A1 | 11/2008 | Williams et al. |

OTHER PUBLICATIONS

Author Unknown, International Neuro Products, "Embolic Coils", 2010 ev3 Inc., pp. 1, http://www.ev3.net/neuro/intl/embolic-coils/nxt-detachable-coils5391.htm.

Author Unknown, Micrus Endovascular, "Enhanced Embolic Coils for the Treatment of Cerebral Aneurysms," 2010, pp. 3, http://www.micrusendovascular.com/products/cerebyte_intl.asp?ln=h.

Author Unknown, NeuroVasx, ePAX, www.neurovasx.com, pp. 1, http://www.neurovasx.com.

Author Unknown, MicroVention Terumo, "The Facts About HydroCoil," pp. 2.

Author Unknown, MicroVention Terumo, "HydroSoft," pp. 2 http://www.microvention.com/Products/tabid/61/Default.aspx.

Author Unknown, MicroVention Terumo, "MicroPlex Coil System," pp. 1.

Author Unknown, "Shape Memory Therapeutics Receives Texas Emerging Technology Fund Award," Biomedical Engineering, Texas A&M University, Oct. 21, 2009, pp. 2.

Boston Scientific, "Brain Aneurysm Treatment," 2010, pp. 2.

Boston Scientific, "0.18" and 0.035" Fibered Platinum Coils," pp. 1.

Boston Scientific, "Matrix2 Detachable Coils," pp. 8.

Boston Scientific, "Neurovascular Intervention," pp. 2.

Boston Scientific, "VortX 18 and 35 Vascular Occlusion Coils," pp. 2.

Denardo, Luigi, et al., "Shape memory polymer foams for cerebral aneurysm reparation: Effects of plasma sterilization on physical properties and cytocompatibility," Acta Biomaterialia 5 (2009) pp. 1508-1518.

Hampikian, Janet M., et al., "Mechanical and radiographic properties of a shape memory polymer composite for intracranial aneurysm coils," Materials Science and Engineering C 26 (2006), pp. 1373-1379.

Heaton, Brian C., "A Shape Memory Polymer for Intracranial Aneurysm Coils: An Investigation of Mechanical and Radiographic Properties of a Tantalum-Filled Shape Memory Polymer Composite," Georgia Institute of Technology, Jul. 2004, pp. 1-60.

Maitland, Duncan J., et al., "Photothermal properties of shape memory polymer miro-actuators for treating stroke," Las. Surg. Med., vol. 30, No. 1, pp. 1-11, 2002.

Maitland, Duncan J., et al., "Prototype laser-activated shape memory polymer foam device for embolic treatment of aneurysms," Journal of Biomedical Optics, May/Jun. 2007, vol. 12(3), pp. 030504-1-3.

Maitland, Duncan J., et al., "Design and Realization of Biomedical Devices Based on Shape Memory Polymers," Materials Research Society, 2009 Spring.

Metzger, M.F., et al., "Mechanical properties of mechanical actuator for treating ischemic stroke," Biomed. Microdevices, vol. 4, No. 2, pp. 89-96, 2002.

Small, Ward IV, et al., "Biomedical applications of thermally activated shape memory polymers," J. Mater. Chem., 2010, 20, pp. 3356-3366.

University of California, Davis, "Development of aneurysm treatment using laser-deployed shape memory polymer foams," http://cbst.ucdavis.edu/research/aneurysm-treatment, pp. 3.

Wilson, Thomas S., et al., "Shape Memory Polymer Therapeutic Devices for Stroke," Proc. of SPIE vol. 6007, pp. 60070R-1-8.

* cited by examiner

SHAPE MEMORY POLYMER PROSTHETIC MEDICAL DEVICE

CROSS REFERENCE TO RELATED APPLICATIONS

This application claims the benefit of priority pursuant to 35 U.S.C. §119(e) of U.S. provisional application No. 61/109,295 filed 29 Oct. 2008 entitled "Shape memory polymer venous valve," which is hereby incorporated herein by reference in its entirety.

STATEMENT REGARDING FEDERALLY SPONSORED RESEARCH OR DEVELOPMENT

This invention was made with government support under grant number EB004481 awarded by the National Institutes of Health. The government has certain rights in the invention.

BACKGROUND

General venous disease affects almost 30% of the US adult population, with incidence increasing as the population ages. Of this population, approximately 2-5% have problems with venous valve incompetence, referred to as Chronic Venous Insufficiency (CVI), which lead to serious conditions including venous ulcers requiring long term treatment with only limited success.

The venous valves are bicuspid valves found primarily in the lower limbs; these act as one-way pressure regulators to ameliorate the effects of gravity-induced hydrostatic blood pressure, especially in the standing position where pressures of over 90 mm Hg can be experienced. Incompetence of these valves can be caused by a variety of factors related to aging, diabetes and hypertension, including deep vein thrombosis, etc. The primary means of treating venous valve incompetence currently involve external lower-limb constriction via a tight-fitting "sock" worn over the lower limb and knee or surgical reconstruction or replacement of the veins in cases of significant deterioration. Both methods are prone to significant problems. The "sock" method is not fully effective since the levels of pressure required to sufficiently compress a deep vein located within strong skeletal musculature are usually far too high to be well-tolerated. Further, patient compliance with this method is usually poor. The surgical reconstruction method may produce good results but is highly invasive, which can be problematic given the typically older and frailer patient that manifests this disease, and expensive.

The most intensive treatment need is for patients with non-healing, chronic venous ulcers. It has been estimated that 2.5 million people have CVI in the United States, and of those, 20% develop venous ulcers. Annually, approximately 1 million procedures for venous ulceration involving large deep veins and deep vein thrombosis are performed in the US. The number of procedures is expected to grow at double-digit rates over the next 10 years. However, the overall prognosis of venous ulcers is poor, with delayed healing and recurrent ulceration being common. More than 50% of venous ulcers require prolonged therapy lasting up to a year or more representing a significant burden on patients, care-givers, and insurers.

The socioeconomic impact of venous ulceration is dramatic, resulting in an impaired ability to engage in social and occupational activities, thus reducing the quality of life and imposing financial constraints. Disability related to venous ulcers leads to loss of productive work hours, estimated at 2 million workdays/year, and may cause early retirement, which is found in up to 12.5% of workers with venous ulcers. The financial burden of venous ulcer disease on the healthcare system is readily apparent. An estimated $1 billion is spent annually on the treatment of chronic wounds in the United States, or up to 2% of the total healthcare budget in all Western countries, and recent estimates place the cost of venous ulcer care at $3 billion annually.

The information included in this Background section of the specification, including any references cited herein and any description or discussion thereof, is included for technical reference purposes only and is not to be regarded subject matter by which the scope of the invention is to be bound.

SUMMARY

A medical device uniquely comprised of a biological tissue combined with a shape memory polymer structure may be used as a circulatory valve prosthesis. The biological tissue (animal or human) provides an in-situ physiological function of the device. The shape memory polymer (SMP) uniquely provides a capability for minimizing the device profile during insertion (e.g., minimally invasive) and then deploying after placement into a memory shape that achieves suitable mechanical structure and stability within the anatomical lumen or cavity. This configuration may be applied to various prosthetic devices including aortic, mitral, and tricuspid valves in the heart; venous valves; anti-reflux valves for the lower esophageal sphincter; and other biological valve structures.

For CVI treatment, an implementation of such a medical device comprises a prosthetic venous valve that is composed of a biological venous valve located within a shape memory polymer housing. Prosthetic venous valves are intended to treat a variety of venous incompetence conditions; however, there are currently no trans-catheter deliverable venous valves on the market. Prosthetic venous valves have particular requirements that are different from conventional trans-catheter delivered valves intended to treat cardiac valve incompetence. These requirements include the ability to be placed in small vessels through flexible catheters while minimizing the potential for vascular dissection given the relatively thin and fragile wall of the vein. These valves must be flexible to pass through a tortuous path to reach the deployment site while exhibiting gentle self-expansion to minimize chances of vessel damage during delivery. Additionally, these valves must adapt to large changes in vessel diameter as is common for large veins in the body requiring a greater degree of compliance in the housing of the valve than available in other prosthetic valves (e.g., cardiac valves). The combination of a shape memory polymer valve housing combined with a biological venous valve provides a solution to these issues.

Bovine jugular vein valves are extracted, fixed using conventional fixation techniques, and sterilized. These valves are then attached to stents manufactured from the shape memory polymers. Attachment mechanisms may comprise mechanical attachment (sewing and/or mechanical trapping), adhesive attachment using glues, insertion of the biological tissue into a mold and polymerizing the shape memory polymer around it, or a combination of these methodologies. The shape memory polymer stents may be in the form of hollow cylinders, which may be slit along the longitudinal axis, fenestrated, or shaped like coils. These flexible structures are intended to allow the stent to be compressed to a smaller diameter during insertion and then recover to its memory shape, providing gentle but sufficient radial force against the vessel/cavity wall.

Hybrid tissue/SMP devices provide substantial improvement over current endovascular treatment devices. The approach disclosed herein allows the device design to utilize thinner components than with other prosthetic valves allowing the total size of the device to be significantly reduced, while increasing durability of the final product. This specifically allows greater access to smaller vessel applications.

In an alternative implementation, an approach to managing venous insufficiency through a prosthetic, shape memory polymer-based, non-biologic valve is disclosed. This design utilizes the unique capability of the SMP material wherein the deployed shape is highly predictable and precise, described herein as "shape certainty." Through this material advance, very precise and fine features may be designed that return to a desired shape and configuration after being straightened and stretched in a packaged, stored product for an extended period. This embodiment may or may not utilize a biological tissue component.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the claimed subject matter will be apparent from the following more particular written Detailed Description of various embodiments and implementations as further illustrated in the accompanying drawings and defined in the appended claims.

DETAILED DESCRIPTION

Chronic Venous Incompetency (CVI) is a progressively degenerative condition affecting millions of people worldwide. With CVI, varicose and spider veins worsen leading to painful swelling, deep venous valve failure, and chronic non-healing ulcers. The stages of progression along with current treatment options are shown in Table 1 below.

TABLE 1

| | CVI Stage | | | |
| --- | --- | --- | --- | --- |
| | 1. Venous Hypertension | 2. Varicose Veins and Deep Vein | 3. Deep Venous Valve Reflux | 4. Chronic Venous Ulcers Reflux |
| Presentation | Visible varicose veins | Skin changes apparent around ankles and calves | Swelling of the calves | Visible skin ulcers |
| Treatment | compressive stockings limb elevation exercise | Previous list plus: ablation/ stripping anticoagulation surgery | Previous list plus: thrombectomy vena cava filter implantation | Previous list plus: dressings surgery |

Existing treatments (as shown in Table 1) are not meeting physician and patient needs. An effective clinical intervention is clearly needed to avoid and/or allow for healing of chronic ulcers, which can only be achieved by re-establishing proper venous drainage. Treatment should be corrective to minimize dependence on patient compliance, especially with elderly patients. Finally, the treatment needs to be minimally invasive as current surgical procedures have shown relatively high morbidity and long recovery times.

A "trans-catheter-placed" prosthetic venous valve is disclosed herein as an alternative treatment option. The device may be inserted via a flexible catheter through an introducer (e.g., 12 fr) allowing for a retrograde percutaneous entry into the femoral vein near the groin. The prosthetic valve is advanced through a catheter under appropriate image guidance (e.g., fluoroscopy) to the proper location. The valve is released from the catheter and the shape memory polymer (SMP) valve body (or stent) may provide gentle expansion with assured vein fixation to avoid migration. Upon removal of the catheter, flow and valve function may be verified using standard measurement methods. After assurance of placement and function, standard percutaneous access closure techniques are used. This nonsurgical treatment facilitates a minimal patient recovery time. It is anticipated that with the availability of these devices, in multiple sizes, physicians will incorporate transcatheter valve replacement procedures during the earlier identified conditions, recognizing that the progression will continue until corrected.

The prosthetic venous valve and procedure provides a minimally invasive solution to the problem of venous valve incompetence. The challenges of designing a minimally invasive venous valve prosthesis are formidable. Among others, these include the need for a gently self-expanding conduit/body that contains the valve without the risk of dissecting through the fragile vein; the ability of the conduit to conform to the typically large changes in vein size and shape that occur due to leg movement; the need for a fully hemocompatible valve material that will not clot even in the presence of low blood flows; and the ability to deliver the valve using small flexible catheters. These challenges have undermined prior trans-catheter attempts that utilize cardiac valves housed within a rigid metal stent, primarily because metal materials (e.g., stainless steel, cobalt chromium, Nitinol) are not well suited for this highly compliant, fragile, highly deforming, low blood-flow environment. The shape memory polymer systems disclosed herein provide distinct and proven advantages that address each of these problems.

The prosthetic venous valve may be configured in an assembly such that valve function (e.g., low-pressure drop, minimal regurgitation, durability, etc) may be achieved in a device that can be reduced in size for introduction and then self-expanded in place for fixation. It should be noted that several of the prior effort failures have been attributed to the stent interaction with the diseased vessel wall. The use of SMP materials, wherein the material stiffness/softness (e.g., modulus) can be optimized for the application, directly mitigates this challenge. The performance of shape memory polymers has been documented in a variety of cardiovascular devices. This work has established the viability of a shape memory polymer stent devices in vascular applications.

Key features used to define and evaluate the optimal design of a shape memory polymer venous valve include: joinder of biological tissue (e.g., bovine venous valve) and shape memory polymer materials; pre-deployed vs. deployed size and shape; radial contact behavior of the stent form against the vessel; resistance to cyclic deformation; and hemocompability. By sequentially using advanced finite element analysis, in vitro testing and animal evaluation, the large number of possible design combinations may be distilled to the most promising designs in an efficient manner.

Either adhesives alone, mechanical fixation (e.g., suturing, or mechanical trapping) alone, molding the SMP around the biological tissue alone, or a combination of any of these may be used to produce stable methods to attach biological tissue (e.g. bovine venous valves) onto shape memory polymer body structures. Initial testing of an adhesive-based approach to fix bovine jugular vein valves with shape memory polymers has been performed. These tests utilized commercially available adhesives (primarily cyanoacrylates due to their history of biological use) and acrylate-based shape memory polymers. Table 2 describes three typical results of pull-testing for three adhesives and a shape memory polymer coupon, indicating an acceptable maintenance of the tissue-polymer bond when stretched (left), and two typical modes of failure (middle, right).

TABLE 2

| Strain Test Result Type 1 | Strain Test Result Type 2 | Strain Test Result Type 3 |
|---|---|---|
| Outcome: Tissue stretches under load. Bond between tissue and SMP coupon is maintained | Outcome: Tissue fails adjacent to bond with SMP coupon. Bond depth in tissue is insufficient to carry the load. | Outcome: Tissue bond to SMP coupon is maintained but SMP coupon fails under load. |
| Acceptable | Unacceptable | Unacceptable |

Figure 1:
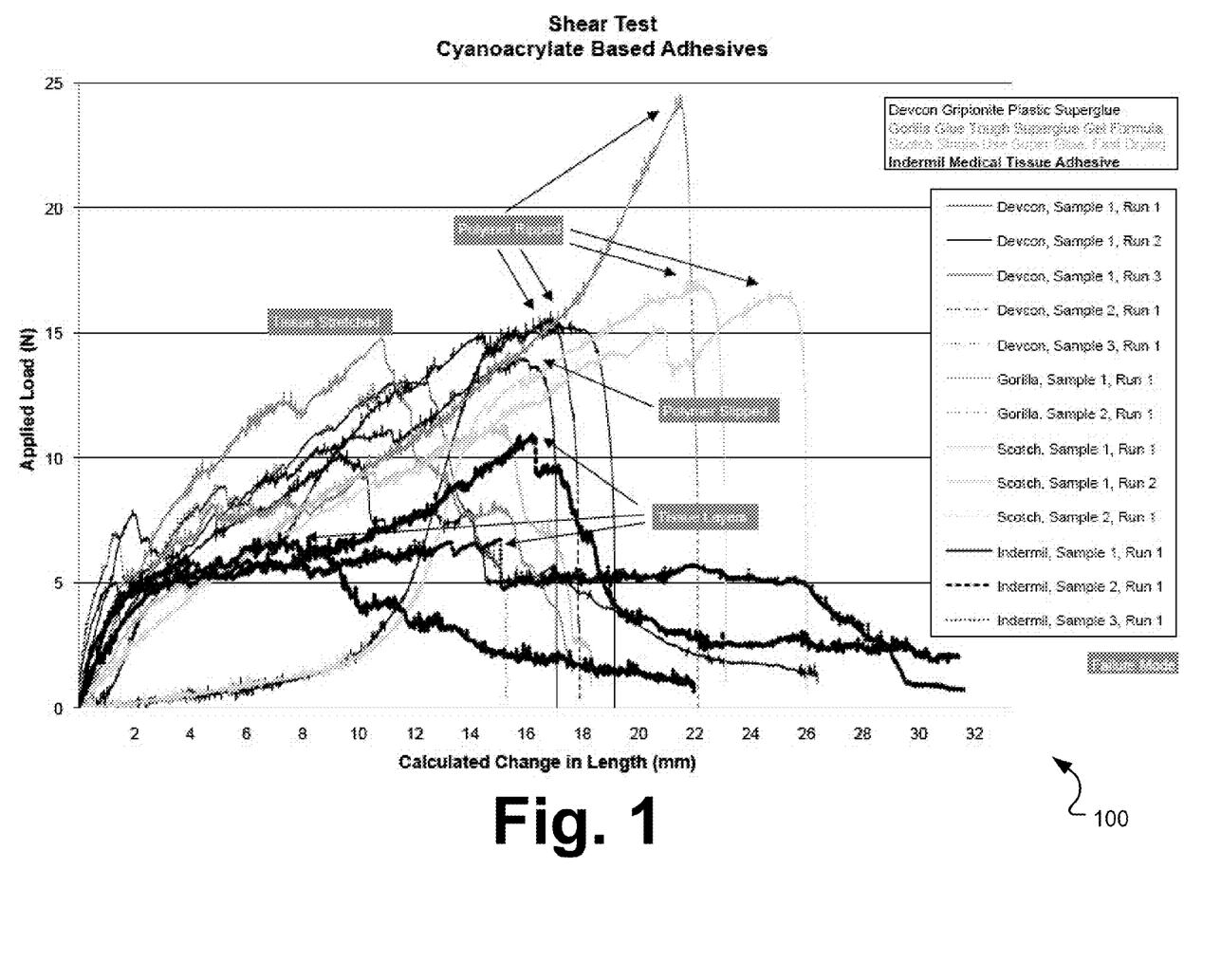
FIG. 1 is a line graph depicting the results of shear tests on biological tissue bonded to a shape memory polymer material with various types of adhesives.

The graph 100 in FIG. 1 summarizes initial key data evaluating strain to failure for several tissue-adhesive combinations using a static pull test of bovine tissue sample joined to an SMP test coupon. These studies have provided important initial information regarding the most promising adhesives that may be useful for a combination biological-tissue and shape memory polymer venous valve. In view of experience with prosthetic cardiac valve development, a combination of both adhesive and mechanical attachment may provide the most stable structure.

An important aspect of medical device design is the ability to perform predictive calculations before implanting a device in an animal model or human subject. Angiographic and MRI imaging of patients may be used to develop three-dimensional computational models of patient-specific anatomy for finite element simulations and virtual surgery. Further these models may be used to fabricate specific prosthetic valve devices from shape memory polymer.

Models have been implemented within the user material subroutine (UMAT) of the finite element software package ABAQUS. Such software models provide the ability to virtually design a variety of shape memory polymer stent configurations that can withstand the typical multi-dimensional deformations seen in large veins while maintaining full conformance to surrounding tissue. These studies allow hundreds of polymer material combinations to be considered in a resource-efficient manner and produce a number of material combinations that are most promising for this application. Devices may then be prototyped using these materials and tested in an in vitro circulatory system for further refinement of device parameters.

The mechanical behavior of shape memory polymer valve stents may be studied using custom-developed, validated, finite element analysis (FEA) software to determine the combination of design features that allow rapid deployment, maintain device shape within tortuous anatomy, and maximize operating endurance. Shape memory polymer devices can be constructed so as to utilize multiple variants of the material formulation within the device allowing for differences in the material properties across various sections of the design. For example, the conduit/stent body may be a relatively soft and compliant material (i.e., having a low modulus of elasticity) to assure gentle expansion and pressure across the contact region. However, the immediate features used to hold the biological tissue to the internal surface of the stent body may be somewhat stiffer (e.g., having a higher modulus of elasticity) to assure good position for coaptation of the valve leaflets for proper valve performance.

Further, individual anchor features located around the perimeter of the stent body, along the proximal and distal edges, may be even stiffer (e.g., having the highest modulus of elasticity relative to the device) to provide suitable anchoring function to avoid migration of the valve in-situ.

Development of a transcatheter delivered SMP venous valve also means that the design may incorporate suitable features and construction to allow it to be compacted or compressed into a pre-deployment shape suitable to travel through or with a catheter passing through an introducer sheath (e.g., 12 fr). In one exemplary configuration, a slit sent, wherein the cylindrical stent body is non-continuous, allows for the stent body to be rolled up with opposing edges along the length of the stent passing over and lying adjacent to each other. In another embodiment the stent may be formed as an open frame or fenestrated cylinder to improve the ability of the device to be compacted. The SMP valve resides within the end of a delivery catheter, constrained by the catheter, to avoid premature shape change before use.

In each embodiment using a combination of biological tissue and shape memory polymer, the biological tissue valve may be positioned and packaged so as not to damage the delicate tissue material and configuration during production and storage. Biological tissues may require storage in a fluid environment to assist in the preservation and storage life. Using a non-reactive shape memory polymer stent body, as opposed to a metal stent, facilitates storing the device in this configuration.

For use, the shape memory polymer venous valve may be delivered to the desired location, chosen by the physician, via a flexible catheter through a percutaneous introducer. Placement is simple by pushing the valve out of the distal end of the delivery catheter into the vasculature. The temperature stimulus of body heat within the blood stream activates the shape memory polymer transition causing the valve stent/body to expand and gently conform to the vessel size at the deployment location.

Because shape memory polymers can be formulated for optimized material softness/stiffness (i.e., the modulus of elasticity), the stent body may be configured to remain compliant after deployment. This compliance facilitates the ability of the valve to remain in position and continuously function before, during, and after the vein dilates and contracts due to normal patient leg movement. A non-compliant system would suffer migration and/or stent fatigue/fracture and/or valve failure under these conditions. This compliant system specifically allows for high cyclic repetition of deformation in-situ without loss of valve function.

Hemocompatibility is demonstrated through the use of properly preserved biological tissue. A prosthetic venous valve is challenged with a low and inconsistent venous blood flow rate. Semi-stagnant blood can be difficult to maintain without clotting. Shape memory polymers have been demonstrated to have excellent hemocompatibility for intravascular use. Further the use of a moldable shape memory polymer for the body allows for optimizing edge and surface configurations to reduce eddy currents and pooling that can be associated with increased thrombogenic activity.

Figure 2:
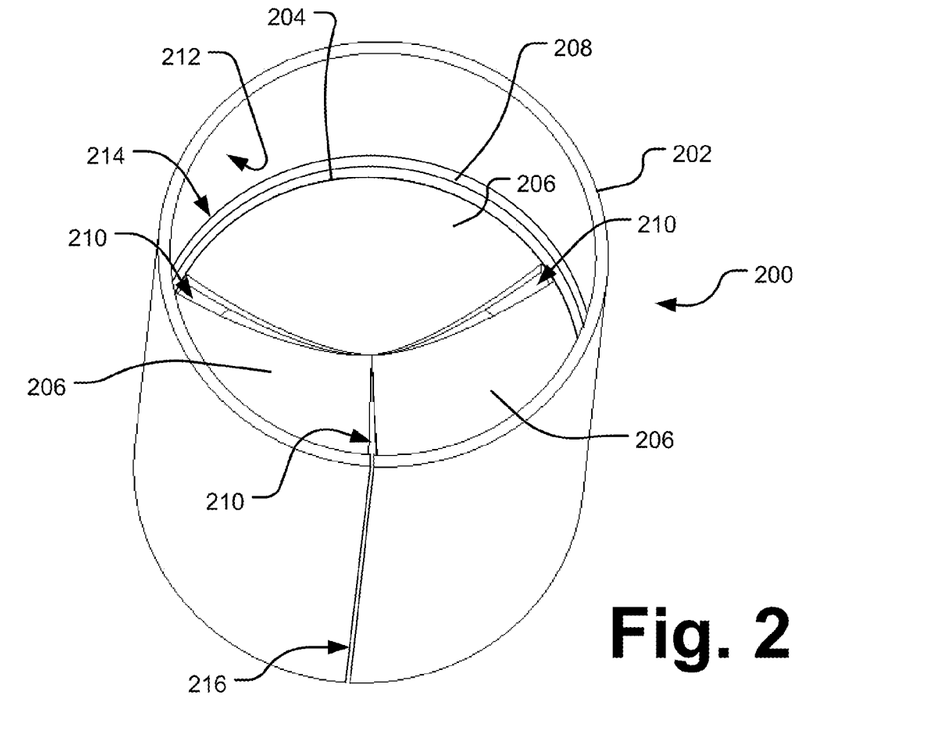
FIG. 2 is an isometric view of an implementation of a prosthetic venous valve formed from a shape memory polymer stent and a biological valve attached thereto.
Figure 3:
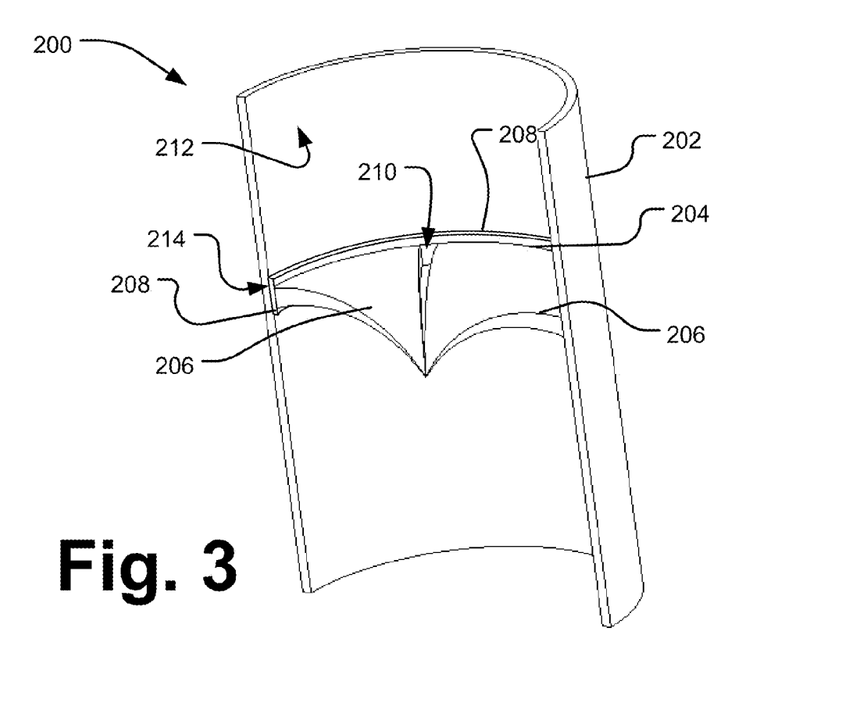
FIG. 3 is an isometric view in cross section of the prosthetic venous valve of FIG. 2.

FIGS. 2 and 3 depict an exemplary embodiment of a prosthetic venous valve 200 incorporating a harvested biologic valve 204 (e.g., a bovine venous valve) within an SMP stent 202. The biologic valve 204 may be harvested as a section of vein including the valve structure. Therefore, the biologic valve 204 includes valve flaps 206 extending from the sidewall 208 of the section of harvested vein. The valve flaps 406 may or may not completely coapt and may be slightly separated from each other adjacent the venous wall 208 by a gap 210. The biologic valve 204 is inserted within the lumen of the SMP stent 202 and may be attached to an inner wall 212 of the SMP stent 202 at an interface 214 between the outer wall of the biologic vein 208 and the inner wall 212 of the SMP stent 202. The attachment at the interface 214 may be made by any of a number of structures as described above, for example, adhesive, sutures, staples, overmolding, or other methods, or combinations of any of these.

As previously stated, the SMP stent 202 may be configured in any of a number of forms, e.g., as a coil or as a fenestrated structure, in addition to the cylindrical form shown. In the embodiment of FIGS. 2 and 3, the SMP stent 202 is formed as a cylinder with a longitudinal slit 216. The slit 216 is aligned with one of the gaps 210 between the flaps 206 of the biologic valve. The sidewall 208 of the vein is also slit in alignment with the slit 216 in the SMP stent 202. In this manner, the SMP stent 202 may be deformed into a predeployment configuration in which the walls of the SMP stent 202 slide past each other to form a spiral shape of a smaller diameter than the post transition cylinder configuration shown in FIGS. 2 and 3. The smaller diameter, predeployment shape allows the prosthetic venous valve 200 to be easily inserted into and delivered by a catheter for implantation in a patient's vasculature. As part of the design process, the diameter of the prosthetic venous valve 200 is selected to conform to the inner diameter of the patient's vein.

When the compacted SMP stent 202 is exposed to the patient's body temperature, the shape memory polymer material transitions to its memory shape, expanding in diameter to create the cylindrical form of the SMP stent 202. The outer wall of the SMP stent 202 lodges against the walls of the patient's vein such that the lumen of the prosthetic venous valve 200 is coaxial with the lumen of the patient's vein. The SMP stent 202 in the deployed state applies a gentle, radially outward pressure to resist travel within the vein, while simultaneously allowing for the prosthetic venous valve 200 to expand and contract as the patient's vein naturally dilates and constricts.

In alternate implementations, a prosthetic, shape memory polymer, nonbiologic valve is disclosed for treatment of CVI. These designs utilize the advantages of shape certainty of shape memory polymers, i.e., accurate prediction and precision of deployed conditions and dimensions (post shape memory recovery) after being stored in a compacted/stored shape for an extended period. Some implementations may use a "body" of a long helical coil made of a shape memory polymer that, when deployed in a vessel, forms an organized coil shape that is in contact with the vein wall. As a flexible structure, the coil can expand and contract concurrent with the vessel during normal body and leg motion.

Figure 4:
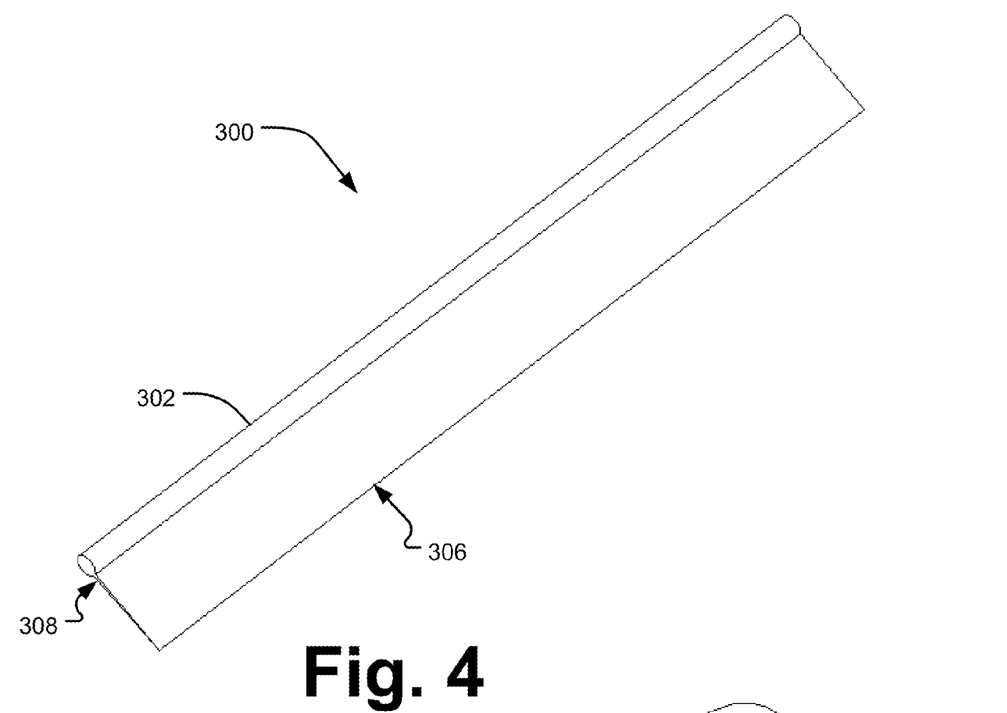
FIG. 4 is an isometric view of an implementation of a shape memory polymer venous valve with a coil stent and a single valve flap in a deformed, pre-transition state.
Figure 5:
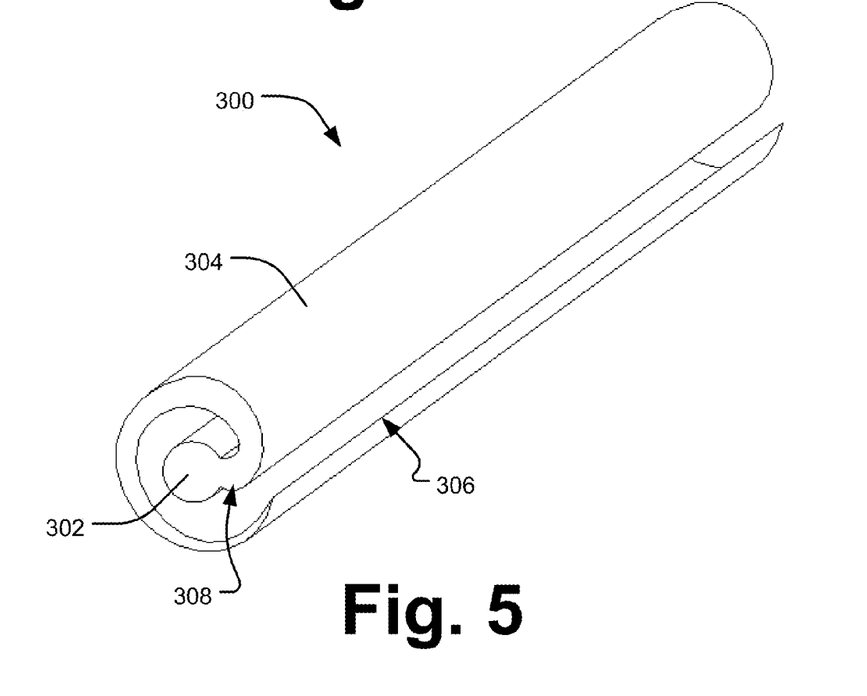
FIG. 5 is an isometric view of the shape memory polymer venous valve of FIG. 4 with the valve flap wrapped around the coil to reduce the diameter of the valve for insertion into a delivery catheter.
Figure 6:
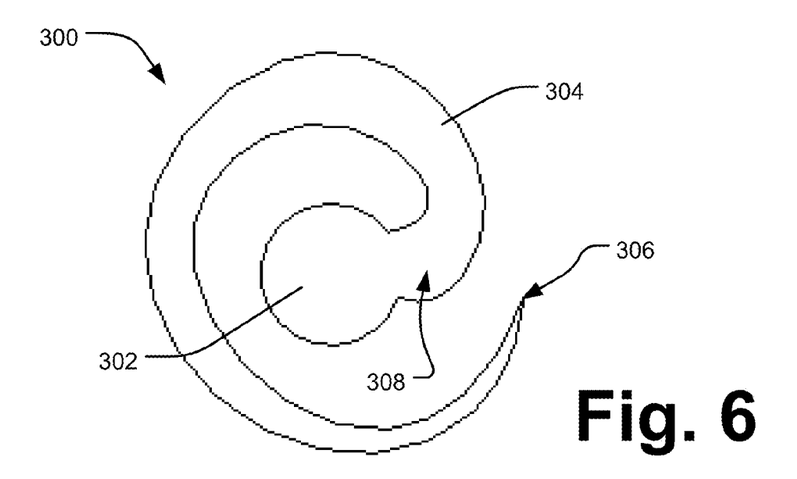
FIG. 6 is an end view of the shape memory polymer venous valve of FIG. 5 in the deformed state.

FIGS. 4-9 depict a first implementation of a prosthetic venous valve comprised entirely of shape memory polymer material. In FIGS. 4 through 6, the SMP venous valve 300 is depicted in its deformed or predeployed state. The SMP venous valve 300 is formed of two primary structures, a coil 302 and a valve flap 304. The valve flap 304 may be viewed as having a leading edge 306 and a flap base 308 where the valve flap 304 is attached to the coil 302. As shown in FIG. 4, the SMP venous valve 300 is in its deformed state, wherein the coil 302 is straightened and the valve flap 304 extends from the coil 302 as a rectangular sheet.

FIGS. 5 and 6 show the SMP venous valve 300 in a configuration used for catheter delivery of the valve 300 into the vein of a patient. In preparation for delivery, the valve flap 304 is wrapped around the linearly extending coil 302 in order to create a quasi-cylindrical configuration for easy insertion into and delivery by a catheter. As seen in FIGS. 5 and 6, the valve flap 304 tapers in thickness from the flap base 308 to the leading edge 306. The flap base 308 is thicker than the leading edge 306 to provide a stronger connective interface between the valve flap 304 and the coil 302, and further to assist in biasing the valve flap 304 to resist retrograde blood flow within the patient's vein. In contrast, the taper to a thinner wall at the leading edge 306 enhances the ability of the valve flap 304 to open wider about a center passageway 310 (see FIG. 7) and allow blood flow through the SMP venous valve 300 in a positive flow direction.

Figure 7:
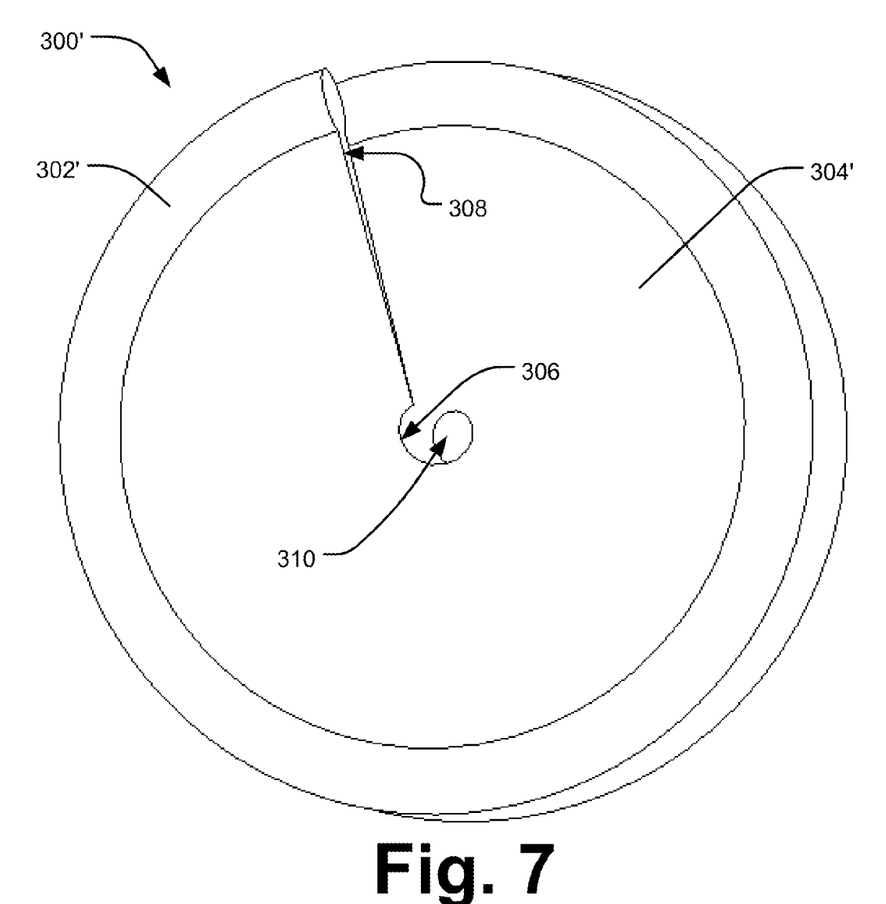
FIG. 7 is an isometric view of the shape memory polymer venous valve of FIG. 4 in a post-transition, memory state forming a coil stent supporting the valve flap radially extending to form a helical web valve structure.
Figure 8:
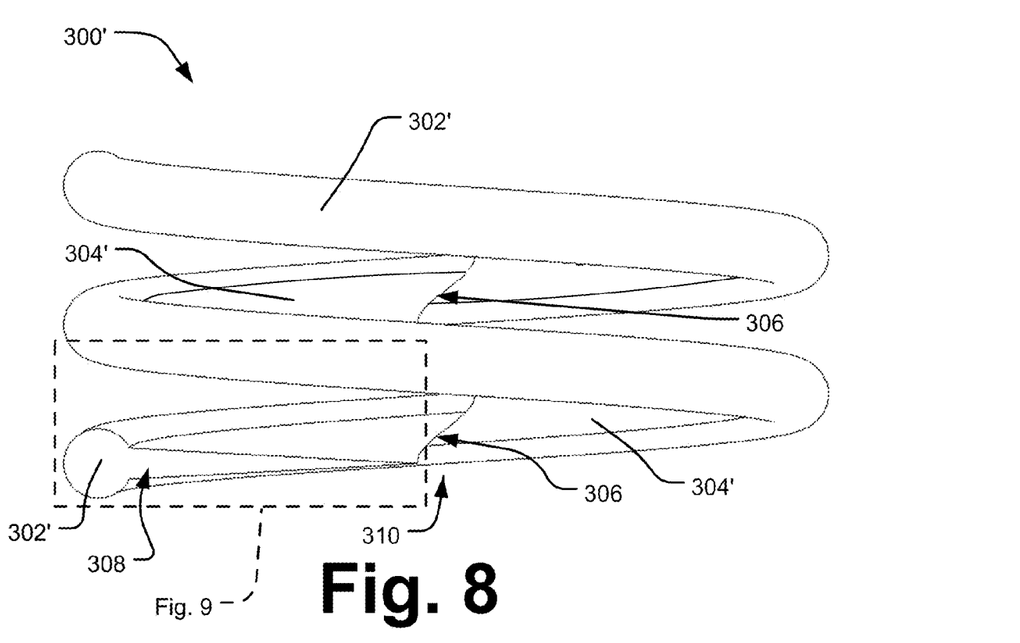
FIG. 8 is a side elevation view of the shape memory polymer venous valve of FIG. 7 in the post-transition, memory state.
Figure 9:
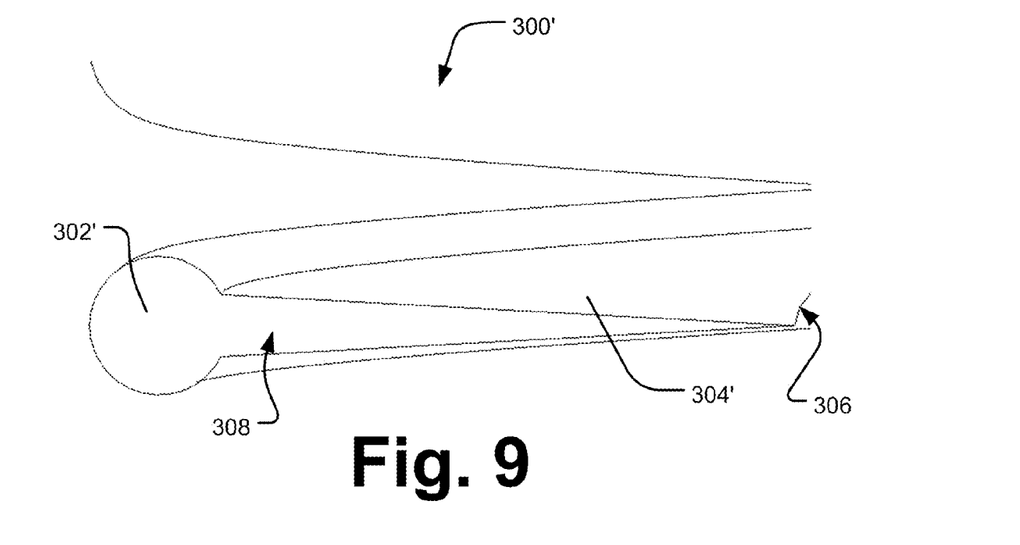
FIG. 9 is an enlarged view of the shape memory polymer venous valve as indicated in FIG. 8.

FIGS. 7-9 depict the SMP venous valve 300' in a deployed or post-transition configuration. When the SMP venous valve 300' is delivered within the vein of a patient via a catheter, the patient's body temperature initiates the transition of the shape memory polymer material from its deformed state as shown in FIGS. 4-6 to its memory state. Upon heating, the SMP venous valve 300' forms a spiral shape supported by the coil 302'. The valve flap 304' extends radially inwardly from the coil 302 to form a helical web structure within the center of the coil 302'. The leading edge 306 of the valve flap 304' defines a center passageway 310 around the center axis of the coil 302'. The center passageway 310 ensures some volume of direct axial blood flow through the SMP venous valve 300' at all times. As shown in greater detail in FIGS. 8 and 9, in the deployed or memory state of the SMP venous valve 300', the valve flap 304' extends radially inwardly from the coil 302' instantaneously following the helical path of the coil 302'. Through a combination of the radial orientation of the valve flap 304' and the thickness of the flap base 308 tapering toward the leading edge 306, the valve flap 304' is biased against retrograde blood flow within the vein while simultaneously pliable toward the leading edge 306 to allow enlargement of the center passageway 310 under conditions of positive directional pressure of the blood flow.

Figure 10:
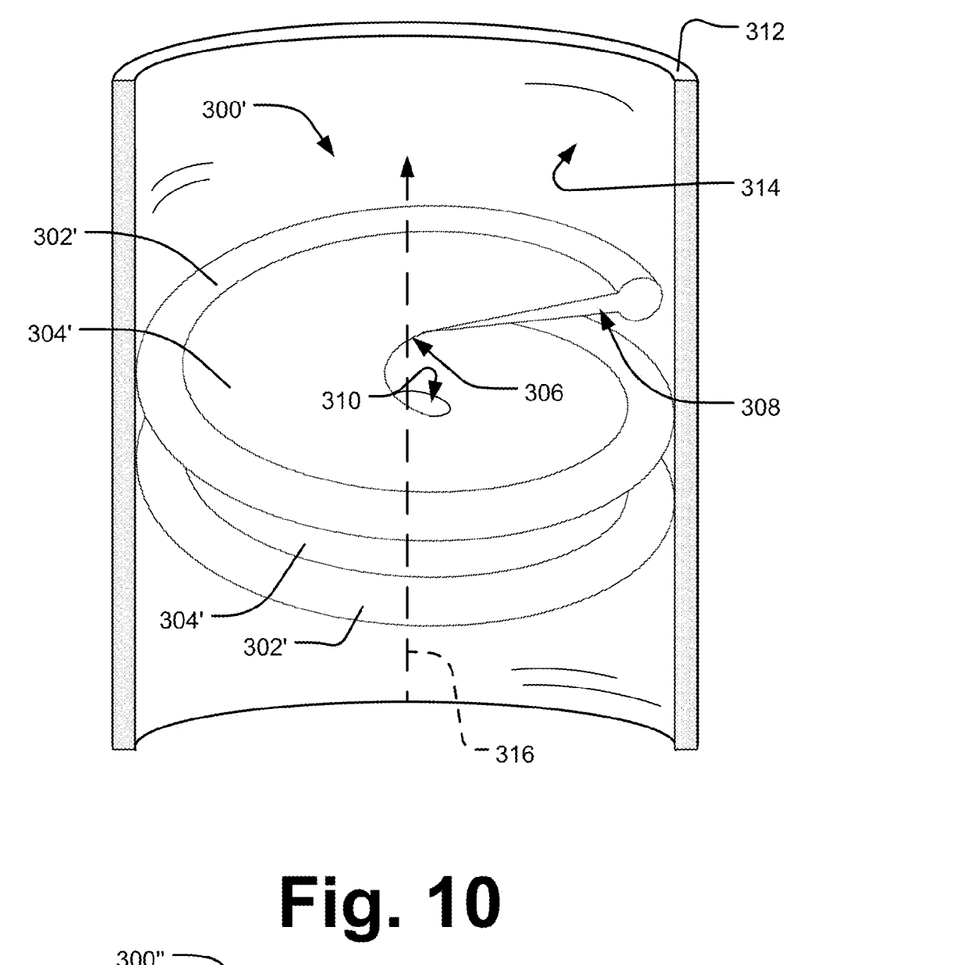
FIG. 10 is an isometric view of the shape memory polymer venous valve of FIG. 7 positioned in a vascular lumen, which is shown in partial cross section.

FIG. 10 depicts a deployed SMP venous valve 300' positioned within the walls of a vein 312. The outside edge of the coil 302' interfaces with the inner wall 314 of the vessel 312. The direction of positive blood flow within the vein 312 is indicated via arrow 316. As depicted in FIG. 10, the SMP venous valve 300' fills the lumen of the vein 312 as an outer edge of the coil 302' interfaces with the inner wall. As previously noted, SMP materials may be formulated to have an appropriate modulus of elasticity in order to radially expand and contract and thereby remain in position as the vein 312 naturally dilates and constricts.

Figure 11:
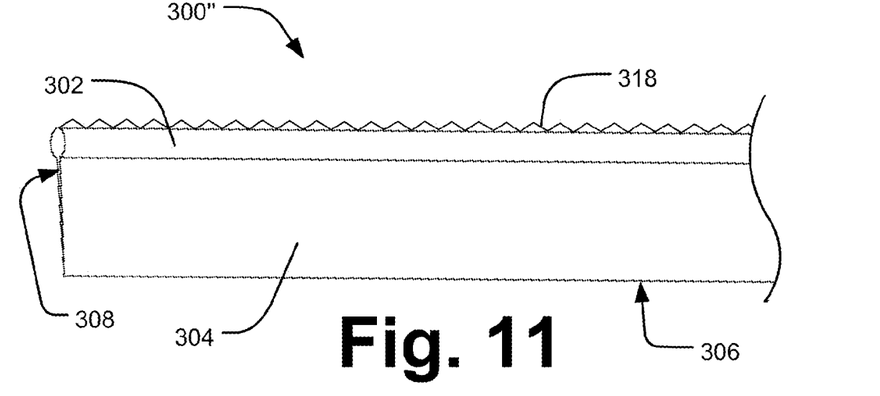
FIG. 11 is an isometric view of a portion of an alternate implementation of a shape memory polymer venous valve with a coil stent and a single valve flap in a deformed, pre-transition state having an additional anchor structure on the coil stent.

An alternate implementation of an SMP venous valve 300" is depicted in FIG. 11 in a deformed or predeployed state. As in the previous embodiment, the SMP venous valve 300" is formed of a coil 302 and a valve flap 304 having a leading edge 306 and a flap base 308. Additionally, the SMP venous valve 300" of FIG. 11 is formed with anchor features along an outside edge of the coil extending generally radially outward and opposite the direction of extension of the valve flap 304. The anchor features 318 may take any of a number of forms including, for example, a roughened surface, a series of bumps, a series of barbs, or any other features that would assist in maintaining an interface between the coil 302 and an inner wall of a blood vessel post-deployment and thus reduce the likelihood of travel by the SMP venous valve 300" within the blood vessel.

Figure 12:
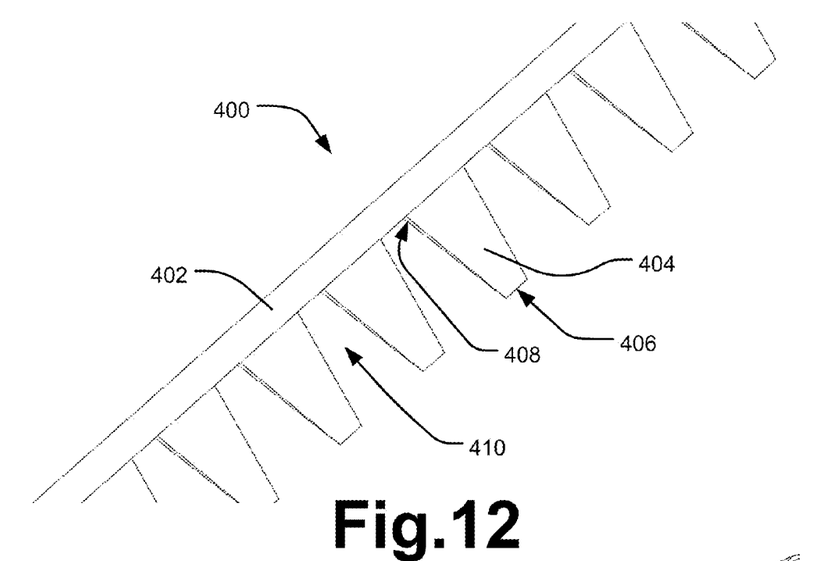
FIG. 12 is an isometric view of a portion of another implementation of a shape memory polymer venous valve with a coil stent and a plurality of valve leaflets in a deformed, pre-transition state.
Figure 13:
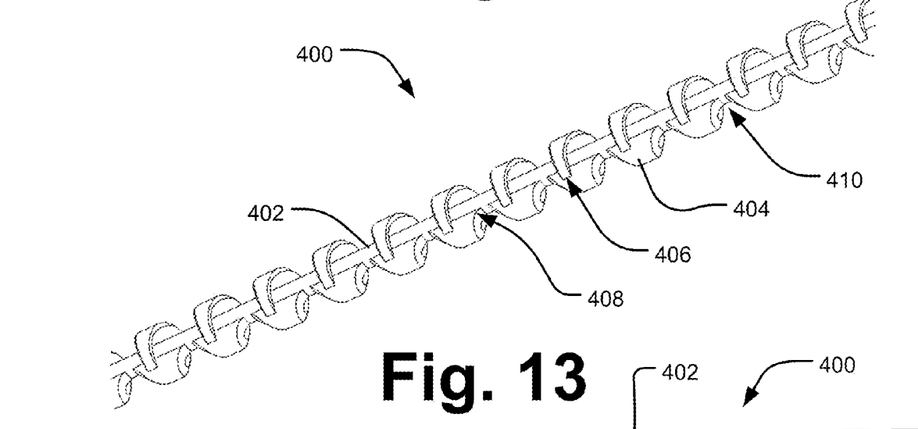
FIG. 13 is an isometric view of a portion of the shape memory polymer venous valve of FIG. 12 with a coil stent and a plurality of valve leaflets wrapped around the coil to reduce the diameter of the valve for insertion into a delivery catheter.
Figure 14:
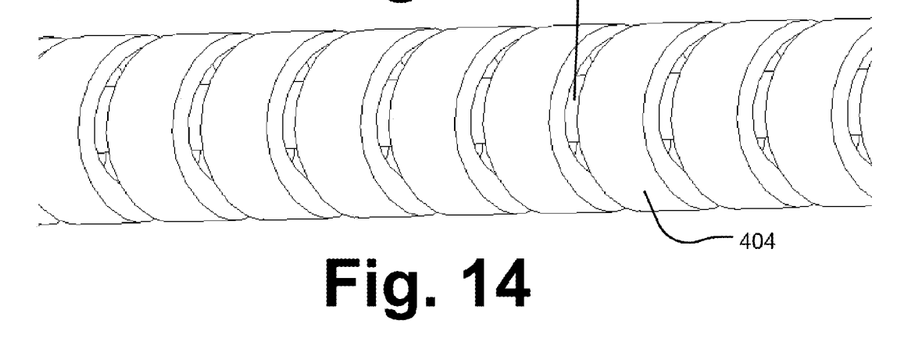
FIG. 14 is an enlarged isometric view of the shape memory polymer venous valve of FIG. 12 from an opposing side.

FIGS. 12-16 depict another implementation of a SMP venous valve 400. In FIGS. 12-14 the SMP venous valve 400 is depicted in its deformed or predeployment configuration. Similar to prior embodiments, the SMP venous valve 400 is formed of a coil 402 that is configured in a straight, linear orientation in the deformed, predeployment state. A series of valve leaflets 404 extend from the sidewall of the coil 402. Each valve leaflet 404 has a leading edge 406 and a leaflet base 408 where the valve leaflet 404 is attached to the coil 402. The valve leaflets 404 extend from the coil 402 similar in formation to pennant flags wherein each of the bases 408 of the leaflets 404 lies within the same plane. The valve leaflets 404 are trapezoidal in shape and taper in width from the leaflet base 408 to the leading edge 406. The valve leaflets 404 additionally taper in thickness from the leaflet base 408 to the leading edge 406. The valve leaflets 404 are also spaced apart from each other along the sidewall of the coil 402, thereby defining a gap 410 between adjacent pairs of valve leaflets 404.

In order to aid delivery of the SMP venous valve 400 through a catheter into a blood vessel of the patient, the valve leaflets 404 may be wrapped around the coil 402 in either a clockwise or counterclockwise direction, and preferably in a uniform direction, as shown in FIGS. 13 and 14. In this way the predeployed SMP venous valve 400 forms a quasi-cylindrical shape that is easily inserted within and delivered by a catheter for delivery and placement of the SMP venous valve 400 within a patient's vasculature.

Figure 15:
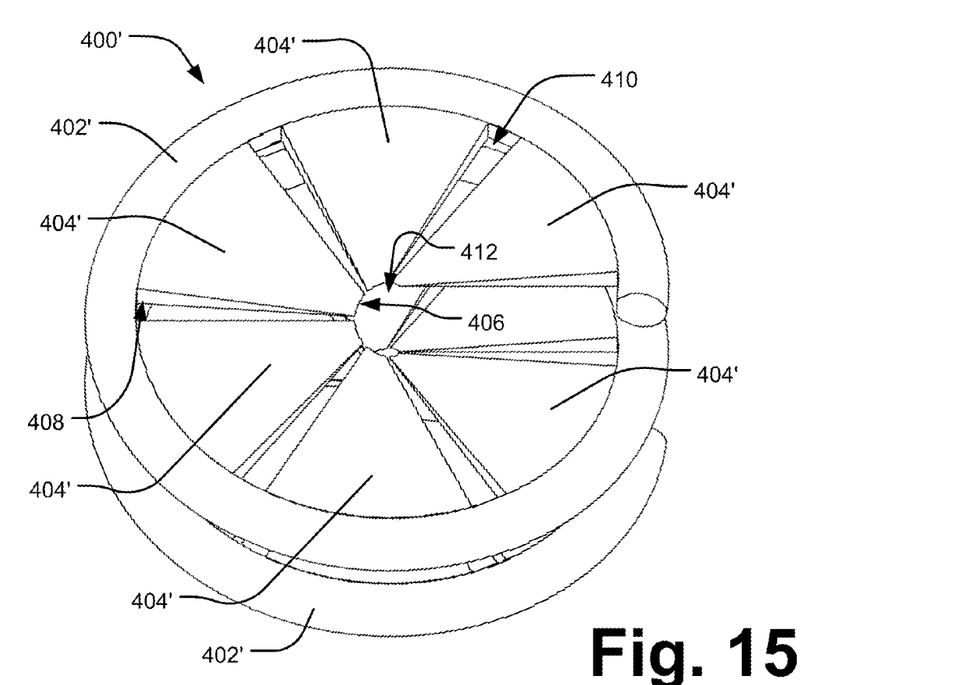
FIG. 15 is an isometric view of the shape memory polymer venous valve of FIG. 12 in a post-transition, memory state forming a coil stent supporting the plurality of valve leaflets radially extending to form a helical valve structure.
Figure 16:
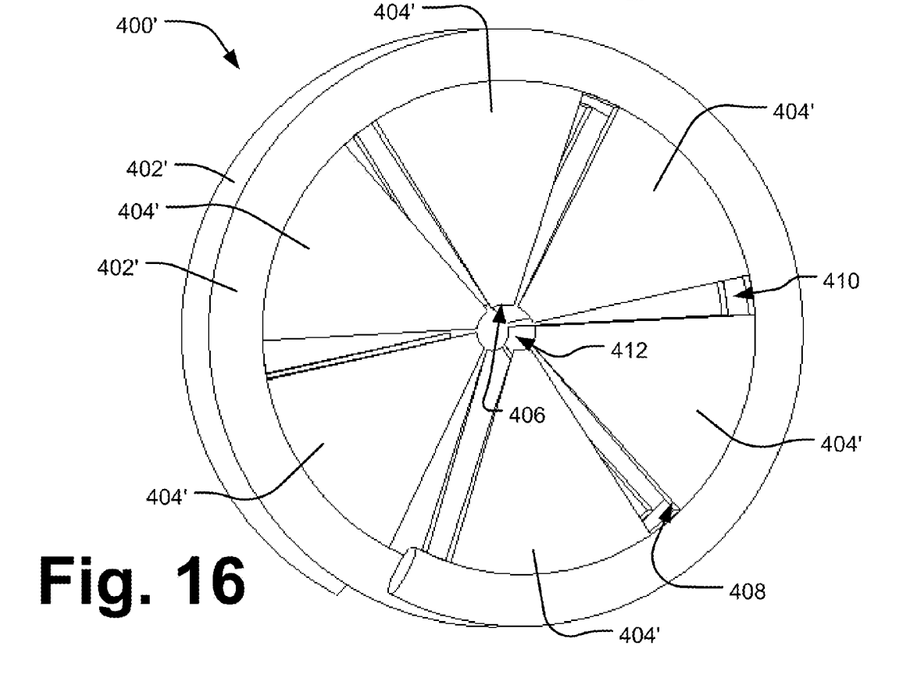
FIG. 16 is an alternate isometric view of the shape memory polymer venous valve of FIG. 15 in the post-transition, memory state.

The deployed or post-transition form of the SMP venous valve 400' is shown in FIGS. 15 and 16. Upon encountering the body heat of a patient after discharge from a catheter, the SMP venous valve 400 transforms from the deformed state to its memory state and forms a coiled valve structure within the patient's vein. The coil 402' spirals against the inner wall of the vein and fits snugly therein. Each of the valve leaflets 404 extends radially inwardly from an inner edge of the coil 402 to partially occlude the lumen of the vein. The valve leaflets may or may not coapt across the lumen, but provide a low (<5 mm Hg) pressure gradient in one direction (forward) of blood flow and a substantially larger (>30 mm Hg) pressure gradient in the opposite direction (reverse) of blood flow such that the deployed (implanted) SMP venous valve 400' device provides minimal resistance to blood flow in the forward direction, but substantial resistant to blood flow in the reverse direction.

In FIGS. 15 and 16, pairs of adjacent valve leaflets 404 remain separated by the gap 410 allowing some volume of blood flow at all times. The leading edges 406 of the valve leaflets 404' define a circular center passageway within the SMP venous valve 400'. This center passageway 412 further allows for a volume blood to flow through the SMP venous valve 400' at all times. However, the radially inward orientation of the valve leaflets 404' and the bias afforded the valve leaflets 404' by the thickened leaflet base 408 and the coil 402', maintain the relatively planar configuration of the valve leaflets 404' under retrograde pressure of the blood volume in the patient's vein, while alternatively allowing the leading edges 406 of the valve leaflets 404 to bend and enlarge the center passageway 412 under positive pressure in the forward direction of blood flow.

These prosthetic venous valve devices may be placed serially in a vessel, using multiple devices along the course of a vein to develop sufficient flow dynamics to restore venous valve functionality. A plurality of these devices, with each device producing a certain degree of forward/reverse pressure gradient (or resistance to blood flow), will work in concert such that the totality of the blood flow resistance is equal to or greater than a single venous valve with leaflets, providing equivalent functionality. The coils in any embodiment may be constructed with a variety of protrusions along its exterior wall in contact with the vessel wall to help anchor the annular portion of the valve and minimize migration. Further, based upon the material properties of the shape memory polymer coil, the shape memory polymer valve devices allow for simple catheter removal by withdrawing the coil and leveraging the natural rubbery elasticity of the shape memory polymer material in its post-deployed configuration.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples, and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A method for making a prosthetic venous valve medical device comprising
    configuring a prosthetic body from a material comprising a shape memory polymer in a first, post-transition, coil form designed to fit snugly against a wall of an anatomical venous lumen, wherein the prosthetic body further comprises
        an outer body defining an interior lumen; and
        a plurality of valve flaps attached to the outer body within the interior lumen at multiple locations along a length of the coil form and arranged to resist retrograde fluid flow within the interior lumen; and
    deforming the prosthetic body by elongating the coil form into a second, linear, pre-transition form that comprises a compact shape or profile relative to the first form for insertion into a delivery device for in vitro placement of the prosthetic medical device.

2. The method of claim 1, wherein
    the valve flaps comprise a biological tissue; and
    the method further comprises affixing the biological tissue to the outer body within the lumen.

3. The method of claim 2, wherein the affixing operation further comprises affixing the biological tissue to the shape memory polymer body with an adhesive.

4. The method of claim 2, wherein the affixing operation further comprises polymerizing the shape memory polymer material around the biological tissue during the configuration operation.

5. The method of claim 2, wherein the affixing operation further comprises mechanically fastening the biological tissue to the prosthetic body with a mechanical fastener.

* * * * *